United States Patent
Jaworowicz et al.

(10) Patent No.: US 6,296,842 B1
(45) Date of Patent: Oct. 2, 2001

(54) PROCESS FOR THE PREPARATION OF POLYMER-BASED SUSTAINED RELEASE COMPOSITIONS

(75) Inventors: Warren E. Jaworowicz, Boxboro; James I. Wright, Lexington, both of MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/638,165

(22) Filed: Aug. 10, 2000

(51) Int. Cl.$^7$ ............................... C08J 9/36; C08J 9/38; C08J 9/40
(52) U.S. Cl. ..................... 424/78.02; 424/17; 424/29; 424/31; 424/35; 424/37; 424/469; 521/64; 521/182; 521/918
(58) Field of Search ............................ 424/78.02, 78.17, 424/78.29, 78.31, 78.35, 78.37, 468, 469; 521/64, 182, 918

(56) References Cited

U.S. PATENT DOCUMENTS

| | | | |
|---|---|---|---|
| 2,648,609 | 8/1953 | Wurster | 99/166 |
| 3,089,824 | 5/1963 | Wurster | 167/82 |
| 3,117,027 | 1/1964 | Lindlof et al. | 118/303 |
| 3,196,827 | 7/1965 | Wurster et al. | 118/24 |
| 3,207,824 | 9/1965 | Wurster et al. | 264/117 |
| 3,241,520 | 3/1966 | Wurster et al. | 118/62 |
| 3,253,944 | 5/1966 | Wurster | 117/100 |
| 4,134,742 | * 1/1979 | Schell | 55/16 |
| 4,897,268 | 1/1990 | Tice et al. | 424/422 |
| 5,019,400 | 5/1991 | Gombotz et al. | 424/497 |
| 5,654,010 | 8/1997 | Johnson et al. | 424/502 |
| 5,656,297 | 8/1997 | Bernstein et al. | 424/484 |
| 5,711,968 | 1/1998 | Tracy et al. | 424/487 |
| 5,716,644 | 2/1998 | Zale et al. | 424/497 |
| 5,916,597 | 6/1999 | Lee et al. | 424/501 |
| 5,922,253 | 7/1999 | Herbert et al. | 264/5 |
| 5,945,284 | * 8/1999 | Livak et al. | 536/23.1 |
| 6,045,830 | 4/2000 | Igari et al. | 424/501 |

FOREIGN PATENT DOCUMENTS

WO 96/19201    6/1996   (WO).

OTHER PUBLICATIONS

Jones, D., "Air Suspension Coating for Multiparticulates," *Drug Development and Industrial Pharmacy*, 20(20):3175–3206 (1994).

* cited by examiner

*Primary Examiner*—Morton Foelak
(74) *Attorney, Agent, or Firm*—Hamilton, Brook, Smith & Reynolds, P.C.

(57) ABSTRACT

The invention relates to a sustained release composition and methods of forming and using said composition for the sustained release of biologically active agent. The sustained release compositions of the invention comprise a biocompatible polymer and a biologically active agent characterized by a porous center and a less porous outer layer wherein the center and outer layer consist of essentially the same materials. The sustained release compositions can be prepared by annealing at least a substantial portion of the exterior surface of a polymer/active agent matrix. The compositions which have been annealed exhibit a decrease in the release of agent over the first 24 hours following administration (i.e., reduced burst) and as a result can show an increase in the duration of sustained release thereby providing increased therapeutic benefits.

17 Claims, 5 Drawing Sheets

PROCESS FOR THE PREPARATION OF POLYMER-BASED SUSTAINED RELEASE COMPOSITIONS

BACKGROUND OF THE INVENTION

Many illnesses or conditions require administration of a constant or sustained level of a medicament or biologically active agent to provide the most effective prophylactic or therapeutic effect. This may be accomplished through a multiple dosing regimen or by employing a system that releases the medicament in a sustained fashion.

Systems for delivering sustained levels of medication have employed biodegradable materials, such as polymers, encapsulating the medicament. The use of biodegradable polymers, for example, in the form of microparticles or microcarriers, provides a sustained release of medicaments, by utilizing the inherent biodegradability of the polymer to sustain the release of the medicament. The ability to provide a sustained level of medication can result in improved patient compliance.

Certain methods of fabricating polymer-based sustained release devices comprise the steps of dissolving a polymer in a solvent, adding to the polymer solution the active agent to be incorporated and removing the solvent from the mixture thereby forming a matrix of the polymer with the active agent distributed throughout the matrix.

However, many of these sustained release compositions can exhibit an increased release of biologically active agent over the first twenty-four hours after administration, commonly referred to as a burst. In some instances, this burst can result in an undesirable increase in the levels of biologically active agent and/or minimal release of agent thereafter. Therefore a need exists to exert additional control over release kinetics by, for example, reducing the burst of agent and/or providing an improved release profile.

SUMMARY OF THE INVENTION

The invention is based upon the discovery that the burst of biologically active agent from a sustained release composition can be decreased by annealing a substantial portion of the exterior surface of the sustained release composition. Annealing can be accomplished, for example, by the application of heat or of an annealing solvent, wherein the annealing solvent is a solvent for the polymer of the sustained release composition. The application of heat or annealing solvent can be accomplished, for example, using a fluidized bed system such as the Wurster process.

The invention relates to a sustained release composition and methods of forming and using said composition for the sustained release of biologically active agent. The sustained release composition of the invention comprises a biocompatible polymer and a biologically active agent characterized by a porous center and a less porous outer layer, wherein the outer layer and the center consist of essentially the same materials. The variance in porosity can be achieved by annealing at least a substantial portion of the exterior surface of a solid polymer/active agent matrix.

The sustained release composition exhibits a more favorable release profile than that observed with compositions of the same material but which do not have a center and outer layer of varying porosity as can be achieved through annealing. For example, the sustained release compositions which have been annealed exhibit a decrease in the release of agent over the first 24 hours following administration (i.e., reduced burst) which can in some instances lead to an increase in the duration of sustained release thereby providing increased therapeutic benefits.

An additional advantage of the present invention is that the annealed exterior surface of the sustained release composition, serves as a coating for the composition without the need for an additional coating component in the composition. As a result, the surface can be modified without a reduction in effective drug load or an increase in particle size. In addition, the surface can be rendered smoother and/or more spherical which can in some instances provide for better flowability and injectability of the sustained release composition.

The method of the invention for preparing a composition for the sustained release of a biologically active agent, comprises the steps of:
a) forming a mixture comprising a biologically active agent, a biocompatible polymer, and a polymer solvent;
b) removing the polymer solvent thereby forming a solid polymer/active agent matrix; and
c) annealing at least a substantial portion of the exterior surface of the polymer/active agent matrix.

Annealing can be accomplished for example by the application of heat or an annealing solvent to at least a substantial portion of the exterior surface of the polymer/active agent matrix. The application of heat or annealing solvent can preferably be conducted using a fluidized bed system.

The method can further comprise the step of forming droplets of the mixture prior to removal of the solvent. Further, the method can comprise freezing the droplets prior to removal of the solvent. According to the method of the invention, the droplets can be microdroplets. In a specific embodiment wherein droplets are formed of the mixture and then frozen, the solvent can be removed by an evaporation and/or extraction process. Phase separation is also a suitable method for removing the solvent.

The sustained release composition of the invention comprises a biocompatible polymer and a biologically active agent characterized by a porous center and a less porous outer layer, wherein the outer layer and the center consist of essentially the same materials. In a preferred embodiment, the sustained release composition is in the form of a microparticle. By "essentially the same materials" is meant that the biologically active agent and the biocompatible polymer of the center and outer layer can be the same, and that other components can also be present either in the center or outer layer provided that the component does not function as a coating material. For example, the outer layer may contain a component, such as a solvent, which is an artifact of the process.

The difference in porosity between the porous center and the less porous outer layer can be assessed, for example, by scanning electron microscopy. For example, freeze fracture scanning electron micrographs can be used in identifying the difference in porosity between the less porous outer layer and porous center. In addition, Helium Pycnometery can be used to determine solid density of the annealed and non-annealed composition. The specific surface area of the annealed and non-annealed compositions can also be determined using nitrogen sorption and a comparison made to indicate a less porous annealed composition as noted in the SEMs.

It is understood that the difference in porosity between the center and the outer layer can be in gradient form and that a marked differentiation of where the porous center ends and the less porous outer layer begins may not be present. However, it should be evident that the porosity of the outer layer as a whole is less than the porosity of the center portion as a whole.

In a preferred embodiment, the composition for sustained release of a biologically active agent is prepared according to the method of the invention as described above. In other words, in a preferred embodiment, the composition for the sustained release of biologically active agent is a composition prepared by the method comprising the steps of:

a) forming a mixture comprising a biologically active agent, a biocompatible polymer, and a polymer solvent;

b) removing the polymer solvent thereby forming a solid polymer/active agent matrix; and c) annealing a substantial portion of the exterior surface of the polymer/active agent matrix.

The sustained release composition of the present invention can be used in a method for providing a therapeutically, prophylactically, or diagnostically effective amount of a biologically active agent to a subject for a sustained period having a reduced burst, as compared to the same composition which does not have layers of varying porosity of essentially the same materials, as can be achieved by annealing a substantial portion of the exterior surface. The invention therefore also relates to a method for providing a therapeutically, prophylactically or diagnostically effective amount of a biologically active agent to a subject for a sustained period, having a reduced burst of agent comprising administering a dose of the sustained release composition prepared as described herein to a subject over a therapeutically useful period of time.

Importantly, the sustained release compositions, which can be prepared according to the claimed method, or by other suitable methods, exhibit lower initial release of biologically active agent when compared to the same compositions which do not have a porous center and a less porous outer layer such as can be achieved by annealing the exterior surface of a prepared sustained release composition. In addition, a polymer/active agent matrix once formed can, without isolation, be further processed to prepare a composition for the sustained release of the biologically active agent having a reduced burst without the need for an additional component such as a coating material. Annealing can be accomplished in a time efficient manner, and it is desirable to limit the time period for annealing in order to decrease the likelihood of fusion and deformation of the sustained release composition, as well as to maintain the biological activity of the active agent. The compositions provide increased therapeutic benefits by reducing fluctuations in active agent concentration in blood levels, by providing a more desirable release profile and by potentially lowering the total amount of biologically active agent needed to provide a therapeutic benefit without the need for additional components in the composition. This further control over the release kinetics should allow tailoring of the sustained release compositions to particular needs of specific patient populations.

DETAILED DESCRIPTION OF THE INVENTION

The foregoing and other objects, features and advantages of the invention will now be more particularly described with reference to the accompanying drawings and pointed out in the claims. It is understood that the particular embodiments of the invention are shown by way of illustration and not as limitations of the invention. The principles of the invention can be employed in various embodiments without departing from the scope of the invention. A description of the preferred embodiments of the invention follows.

The method of the invention for preparing a composition for the sustained release of a biologically active agent, comprises the steps of:

a) forming a mixture comprising a biologically active agent, a biocompatible polymer, and a polymer solvent;

b) removing the polymer solvent thereby forming a solid polymer/active agent matrix; and c) annealing at least a substantial portion of the exterior surface of the polymer/active agent matrix.

The method can further comprise the step of forming droplets of the mixture prior to removal of the solvent. Further, the method can comprise freezing the droplets prior to removal of the solvent. According to the method of the invention, the droplets can be microdroplets. In a specific embodiment wherein droplets are formed of the mixture and then frozen, the solvent can be removed by an evaporation and/or extraction process. Phase separation is also a suitable method for removing the solvent.

The sustained release composition of the invention comprises a biocompatible polymer and a biologically active agent characterized by a porous center and a less porous outer layer, wherein the outer layer and the center consist of essentially the same materials. In a preferred embodiment, the sustained release composition is in the form of a microparticle. By "essentially the same materials" is meant that the biologically active agent and the biocompatible polymer of the center and outer layer can be the same. However, other components may be present either in the center or outer layer provided that the component does not function as a coating material. For example, the outer surface layer may contain a component, such as a solvent, which is an artifact of the process.

The difference in porosity between the porous center and the less porous outer layer can be assessed by scanning electron microscopy. For example, freeze fracture scanning electron micrographs can be used in identifying the difference in porosity between the less porous outer layer and porous center.

It is understood that the difference in porosity between the center and the outer layer can be in gradient form and that a marked differentiation where the porous center ends and the less porous outer layer begins may not be present. However, it should be evident that the porosity of the outer layer as a whole is less than the porosity of the center as a whole.

In a preferred embodiment, the composition for sustained release of a biologically active agent comprises a polymer/active agent matrix wherein at least a substantial portion of the exterior surface of the matrix is annealed. The sustained release composition can be prepared according to the method of the invention as described above. In other words, in a preferred embodiment the composition for the sustained release of biologically active agent is a composition prepared by the method comprising the steps of:
  a) forming a mixture comprising a biologically active agent, a biocompatible polymer, and a polymer solvent;
  b) removing the polymer solvent thereby forming a solid polymer/active agent matrix; and
  c) annealing at least a substantial portion of the exterior surface of the polymer/active agent matrix.

The sustained release composition of the present invention can be used in a method for providing a therapeutically, prophylactically, or diagnostically effective amount of a biologically active agent to a subject for a sustained period having a reduced burst. The invention therefore also relates to a method for providing a therapeutically, prophylactically or diagnostically effective amount of a biologically active agent to a subject for a sustained period, having a reduced burst of agent comprising administering a dose of the sustained release composition prepared as described herein to a subject over a therapeutically useful period of time.

As used herein, the term "a" or "an" refers to one or more.

As used herein, the term "microparticles" refers to particles having a volume median particle size of between about 1 and 1000 microns.

As used herein, the term "non-solvent for a substance" refers to a material which does not substantially dissolve that substance.

"Annealing" as that term is used herein refers to treating a substantial portion of the exterior surface of the polymer/active agent matrix by the application of an external stress which increases the fluidity of the surface of the polymer/active agent matrix, and upon rehardening results in a smoother and less porous outer layer for the sustained release composition. The stress can be, for example, heat or an annealing solvent. The annealing solvent is a solvent for the polymer of the polymer/active agent matrix. The heat or annealing solvent can be applied in any suitable manner. For example, heat can be applied using a controlled temperature chamber. Likewise, solvent can be applied in a suitable solvent-containing chamber. Preferably, the application of heat or solvent is accomplished using a fluidized bed system, such as a bottom spray system also referred to in the art as a Wurster system. Other fluidized bed systems such as top spray and rotary spray are also suitable.

In the embodiment wherein annealing is accomplished by the application of heat, the temperature of the heat to which the polymer/active agent matrix is exposed should be above the Tg of the polymer of the polymer/active agent matrix, but below the temperature at which the biologically active agent, which is present in the matrix, will undergo substantial degradation. It is preferred that the temperature be only slightly greater than the Tg of the polymer to avoid creating a polymer surface which is undesirably tacky and can result in clumping of the polymer/active agent matrix. For example, the temperature can be from about 3° C. to about 50° C. above the Tg of the polymer of the matrix. Preferably the temperature is from about 3° C. to about 20° C. above the Tg.

Heat should be applied only for a period of time necessary to achieve the desired level of annealing. Preferably the amount of time is about 5 hours or less. For example, about 3 hours or less, such as between 0.25 hours and 2 hours. It is advantageous to limit the time period for annealing by the application of heat in order to decrease undesirable fusion and deformation of the polymer/active agent matrix.

In the embodiment wherein annealing is accomplished by the application of an annealing solvent, suitable annealing solvents can be determined based on the solubility characteristics of the polymer of the polymer/active agent matrix. For example, the annealing solvent can be the same solvent as used in preparation of the polymer/active agent matrix. The annealing solvent can also be different than the solvent used in preparation of the matrix provided that the fluidity of a substantial portion of the exterior surface of the matrix is increased. Combinations of annealing solvents or cosolvent systems comprising an annealing solvent are also suitable. The temperature at which the solvent is applied should be below the flash point of the solvent but above the freezing point of the solvent.

Suitable annealing solvents for use in the invention include, but are not limited to, methylene chloride, chloroform, acetone, ethyl acetate, anisole, methyl acetate, hexafluoroisopropanol, tetrahydrofuran and dimethylsulfoxide.

In a preferred embodiment, annealing of at least a substantial portion of the exterior surface of the polymer/active agent matrix is performed using a fluidized bed coating system. In a specific embodiment, annealing is accomplished by the application of an annealing solvent in the fluidized bed system. In another embodiment, annealing is accomplished by raising the temperature of the fluidized bed above the Tg of the polymer of the polymer/active agent matrix. The parameters of the fluidized bed process should be such that the heat or annealing solvent are distributed over at least a substantial portion of the exterior surface of the matrix.

In general, a "fluidized bed system" is a process in which a substrate, for example, a drug particle is suspended using air or inert gas thereby creating a fluidized bed of the substrate. The fluidized bed of the substrate, once created can be coated with a desired solution, suspension, emulsion, latex or hot melt. For a general discussion of fluidized bed systems see, Jones, D., "Air Suspension Coating for Microparticulates," *Drug Development and Industrial Pharmacy*, 20(20): 3175–3206 (1994), the entire contents of which is incorporated herein by reference.

As used herein, a "fluidized bed system" is defined as a system in which a polymer/active agent matrix is suspended using air or an inert gas to create a fluidized bed of the matrix, followed by application of an annealing solvent or heat. The annealing solvent is a solvent or a combination of solvents which can solubilize the polymer of the matrix. A cosolvent system comprising a solvent for the polymer of the matrix is also suitable. The heat is applied by increasing the temperature of the fluidized bed above the Tg of the polymer of the matrix. The polymer/active agent matrix can be, for example, in the form of microparticles.

There are three main types of fluidized bed systems. Namely, top spray, rotary spray and bottom spray. The bottom spray system, often referred to as the Wurster system, is a preferred fluidized bed process for use in annealing the exterior surface of the polymer/active agent matrix of the invention. However, any fluidized bed system is suitable. The Wurster process or bottom spray process is fully described in U.S. Pat. Nos. 3,196,827, 3,117,027, 3,207,824, 3,241,520, 2,648,609, 3,253,944, and 3,089,824 to Wurster, the entire content of all of which is hereby incorporated by reference.

The period of time needed to anneal the exterior surface of the polymer/active agent matrix depends in part on the quantity of the matrix to be annealed. That is, the greater the quantity of the matrix to be annealed the longer the process will take for a given set of conditions. For example, when annealing of the exterior surface is accomplished by the application of heat, the temperature of the fluidized bed will impact the period of time necessary to achieve the desired level of annealing. That is, when the temperature at which annealing is conducted is substantially higher than the Tg of the polymer of the matrix, the period of time to achieve the desired level of annealing will be less than when the temperature is just slightly above the Tg of the polymer of the matrix. However, a temperature slightly above the Tg of the polymer is preferred in order to avoid creating a tacky exterior surface. In addition, it is advantageous to limit the period of heat application to avoid fusion and deformation of the polymer/active agent matrix and degradation of the biologically active agent. Preferably the amount of time for the application of heat is about 5 hours or less. For example, about 3 hours or less, such as between 0.25 hours and about 2 hours.

When annealing is accomplished using an annealing solvent, the rate of solvent application to the exterior surface can be adjusted to avoid fusion and deformation of the polymer/active agent matrix.

"Exterior surface", as that term is used herein, is the outermost or external surface of the polymer/active agent matrix. When the matrix is porous and contains spaces which are recessed below the uppermost exterior surface, the surface defining this recessed space is also considered part of the exterior surface. In other words, the exterior surface is the surface in fluid communication with the external enviroment of the matrix.

The quantity of the sustained release composition which is annealed and therefore, the less porous outer layer, can be defined as a % weight of the sustained release composition. Therefore, the thickness of the less porous outer layer, for a certain % weight, depends on the mass of the composition being annealed. The % weight of the sustained release composition which is annealed can be from about 0.05% to about 95%. For example, from about 1% to about 50%, such as from about 5% to about 30%, in particular from about 10% to about 25%.

The term "at least a substantial portion of the exterior surface" as is used herein, refers to about 25% or more of the exterior surface of the polymer/active agent matrix. In a particular embodiment, about 40% or more of the exterior surface is annealed. In a preferred embodiment about 50% or more of the exterior surface is annealed such as between about 50% and 100%, for example between about 60% and 100%. It is understood that the entire exterior surface does not need to be annealed. This is true, in view of the sustained release properties already possessed by the polymer/active agent matrix being annealed. As such, a complete annealing of the exterior surface is not needed to provide a useful and desirable sustained release composition.

As defined herein, a sustained release of biologically active agent is a release of the agent from the sustained release composition of the invention which occurs over a period which is longer than that period during which a biologically significant amount of the agent would be available following direct administration of a solution of the agent. It is preferred that a sustained release be a release of agent which occurs over a period of greater than two days. A sustained release of agent can be a continuous or a discontinuous release, with relatively constant or varying rates of release. The continuity of release and level of release can be affected by the type of polymer composition used (e.g., monomer ratios, molecular weight, block composition, and varying combinations of polymers), protein loading, and/or selection of excipients to produce the desired effect.

Suitable biocompatible polymers, can be either biodegradable or non-biodegradable polymers or blends or copolymers thereof, as described herein. A polymer is biocompatible if the polymer and any degradation products of the polymer are non-toxic to the recipient and also possess no significant deleterious or untoward effects on the recipient's body, such as a significant immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly (lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons. In a preferred embodiment, the polymer is biodegradable polymer or copolymer. In a more preferred embodiment, the polymer is a poly(lactide-co-glycolide)(hereinafter "PLGA") which can have lactide:glycolide ratios of about 25:75, 50:50 and 75:25, and a molecular weight of about 5,000 Daltons to about 70,000 Daltons. In an even more preferred embodiment, the molecular weight of the PLGA used in the present invention has a molecular weight of about 5,000 Daltons to about 42,000 Daltons.

The term "biologically active agent," as used herein, is an agent, or its pharmaceutically acceptable salt, which when released in vivo, possesses the desired biological activity, for example therapeutic, diagnostic and/or prophylactic properties in vivo. It is understood that the term includes stabilized biologically active agents as described herein. A sustained release composition of the invention can contain from about 0.01% (w/w) to about 90% (w/w) of active agent (dry weight of composition). The amount of agent can vary depending upon the desired effect of the agent, the planned release levels, and the time span over which the agent is to be released. A preferred range of agent loading is between about 0.1% (w/w) to about 30% (w/w). A more preferred range of agent loading is between about 0.5% (w/w) to about 20% (w/w) agent.

Examples of suitable biologically active agents include proteins, muteins and active fragments thereof, such as immunoglobulins, antibodies, cytokines (e.g., lymphokines, monokines, chemokines), interleukins, interferons (β-IFN, α-IFN and γ-IFN), erythropoietin, nucleases, tumor necrosis factor, colony stimulating factors, insulin, enzymes (e.g. superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens), antigens, blood coagulation factors; growth factors; peptides such as protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antibiotics such as gentamicin, tetracycline hydrochloride and ampicillin; antipyretic, analgesic and anti-inflammatory agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and sodium heparin; hemostatic agents such as thrombin, menadione sodium bisulfite and acetomenaphthone; antituberculous agents such as isoniazide and ethanbutol; hormones such as prednisolone sodium phosphate and methimazole; antipsychotic agents such as risperidone; and narcotic antagonists such as nalorphine hydrochloride.

In one embodiment, the biologically active agent is stabilized. The biologically active agent can be stabilized against degradation, loss of potency and/or loss of biological activity, all of which can occur during formation of the sustained release composition having the biologically active agent dispersed therein, and/or prior to and during in vivo release of the biologically active agent. In one embodiment, stabilization can result in a decrease in the solubility of the biologically active agent, the consequence of which is a reduction in the initial release of biologically active agent, in particular, when release is from a sustained release composition. In addition, the period of release of the biologically active agent can be prolonged.

Stabilization of the biologically active agent can be accomplished, for example, by the use of a stabilizing agent or a specific combination of stabilizing agents. The stabilizing agent can be present in the mixture. "Stabilizing agent", as that term is used herein, is any agent which binds or interacts in a covalent or non-covalent manner or is included with the biologically active agent. Stabilizing agents suitable for use in the invention are described in U.S. Pat. Nos. 5,716,644, 5,674,534, 5,654,010, 5,667,808, and 5,711,968, and co-pending U.S. patent application Ser. No. 08/934,830 to Burke et al., filed on Sep. 22, 1997 and Ser. No. 09/104,549 to Burke, filed on Jun. 25, 1998 the entire teachings of which are incorporated herein by reference.

For example, a metal cation can be complexed with the biologically active agent, or the biologically active agent can be complexed with a polycationic complexing agent such as protamine, albumin, spermidine and spermine, or associated with a "salting-out" salt. In addition, a specific combination of stabilizing agents and/or excipients may be needed to optimize stabilization of the biologically active agent. For example, when the biologically active agent in the mixture is an acid-stable or free sulfhydryl-containing protein such as β-IFN, a particular combination of stabilizing agents which includes a disaccharide and an acidic excipient can be added to the mixture. This type of stabilizing formulation is described in detail in U.S. Ser. No. 09/501,934, filed on Feb. 10, 2000 the entire content of which is incorporated herein by reference.

Suitable metal cations include any metal cation capable of complexing with the biologically active agent. A metal cation-stabilized biologically active agent, as defined herein, comprises a biologically active agent and at least one type of metal cation wherein the cation is not significantly oxidizing to the biologically active agent. In a particular embodiment, the metal cation is multivalent, for example, having a valency of +2 or more. It is preferred that the metal cation be complexed to the biologically active agent.

Suitable stabilizing metal cations include biocompatible metal cations. A metal cation is biocompatible if the cation is non-toxic to the recipient, in the quantities used, and also presents no significant deleterious or untoward effects on the recipient's body, such as a significant immunological reaction at the injection site. The suitability of metal cations for stabilizing biologically active agents and the ratio of metal cation to biologically active agent needed can be determined by one of ordinary skill in the art by performing a variety of stability indicating techniques such as polyacrylamide gel electrophoresis, isoelectric focusing, reverse phase chromatography, and HPLC analysis on particles of metal cation-stabilized biologically active agents prior to and following particle size reduction and/or encapsulation. The molar ratio of metal cation to biologically active agent is typically between about 1:2 and about 100: 1, preferably between about 2:1 and about 12:1.

Examples of stabilizing metal cations include, but are not limited to, $K^+$, $Zn^{+2}$, $Mg^{+2}$ and $Ca^{+2}$. Stabilizing metal cations also include cations of transition metals, such as $Cu^{+2}$. Combinations of metal cations can also be employed. In a particular embodiment, $Zn^{+2}$ is used as a stabilizing metal cation for rhGH at a zinc cation component to hGH molar ratio of about 4:1 to about 100:1. In a preferred embodiment, the zinc cation component to hGH molar ratio is about 4:1 to about 12:1, and most preferably 10:1.

The biologically active agent can also be stabilized with at least one polycationic complexing agent. Suitable polycationic complexing agents include, but are not limited to, protamine, spermine, spermidine and albumin. The suitability of polycationic complexing agents for stabilizing biologically active agents can be determined by one of ordinary skill in the art in the manner described above for stabilization with a metal cation. An equal weight ratio of polycationic complexing agent to biologically active agent is suitable.

Further, excipients can be added to maintain the potency of the biologically active agent over the duration of release and modify polymer degradation. The excipients can be added to the dispersed system which is then atomized or can be added to the mixture which is subjected to fragmenting either before or after fragmentation of the dried substance to achieve particles of biologically active agent. Suitable excipients include, for example, carbohydrates, amino acids, fatty acids, surfactants, and bulking agents, and are known to those skilled in the art. An acidic or a basic excipient is also suitable. The amount of excipient used is based on its ratio to the biologically active agent, on a weight basis. For amino acids, fatty acids and carbohydrates, such as sucrose, trehalose, lactose, mannitol, dextran and heparin, the ratio of carbohydrate to biologically active agent, is typically between about 1:10 and about 20:1. For surfactants the ratio of surfactant to biologically active agent is typically between about 1:1000 and about 2:1. Bulking agents typically comprise inert materials. Suitable bulking agents are known to those skilled in the art.

The excipient can also be a metal cation component which is separately dispersed within the polymer matrix. This metal cation component acts to modulate the release of the biologically active agent and is not complexed with the biologically active agent. The metal cation component can optionally contain the same species of metal cation, as is contained in the metal cation stabilized biologically active agent, if present, and/or can contain one or more different species of metal cation. The metal cation component acts to modulate the release of the biologically active agent from the polymer matrix of the sustained release composition and can enhance the stability of the biologically active agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3 \cdot Mg(OH)_2 \cdot 5H_2O$), $MgSO_4$, $Zn(OAc)_2$, $Mg(OAc)_2$, $ZnCO_3$ (such as $3Zn(OH)_2 2ZnCO_3) ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to is between about 1:99 to about 1:2 by weight. The optimum ratio depends upon the polymer and the metal cation component utilized. A polymer matrix containing a dispersed metal cation component to modulate the release of a biologically active agent from the polymer matrix is further described in U.S. Pat. No. 5,656,297 to Bernstein et al. and co-pending U.S. patent application Ser. No. 09/056,566 filed on Apr. 7, 1998, the teachings of both of which are incorporated herein by reference in their entirety.

In yet another embodiment, at least one pore forming agent, such as a water soluble salt, sugar or amino acid, can be included in the sustained release composition to modify the microstructure. The proportion of pore forming agent added to the suspension comprising submicron particles of biologically active agent dispersed in a solution comprising at least one biocompatible polymer and at least one polymer solvent, is between about 1% (w/w) to about 30% (w/w). It is preferred that at least one pore forming agent be included in a nonbiodegradable polymer matrix of the present invention.

A number of methods are known by which polymer/active agent matrices can be formed. In many of these processes, the material to be encapsulated is dispersed in a solvent containing a wall forming material. At a single stage of the process, solvent is removed from the microparticles and thereafter the microparticle product is obtained.

For example, methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active agent, a biocompatible polymer and a polymer solvent is processed to create droplets, wherein at least a significant portion of the droplets contains polymer, polymer solvent and the active. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety organic solvent is evaporated from a dispersion of microparticles in an aqueous medium, preferably under reduced pressure.

Similarly, the disclosure of U.S. Pat. No. 3,891,570, incorporated herein by reference in its entirety shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, incorporated herein by reference in its entirety, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

Without being bound by a particular theory it is believed that the release of the biologically active agent can occur by two different mechanisms. First, the biologically active agent can be released by diffusion through aqueous filled channels generated in the polymer matrix, such as by the dissolution of the biologically active agent, or by voids created by the removal of the polymer solvent during the preparation of the sustained release composition. A second mechanism is the release of the biologically active agent, due to degradation of the polymer. The rate of degradation can be controlled by changing polymer properties that influence the rate of hydration of the polymer. These properties include, for instance, the ratio of lactide to glycolide, comprising a polymer; the use of the L-isomer of a monomer instead of a racemic mixture; and the molecular weight of the polymer. These properties can affect hydrophilicity and crystallinity, which control the rate of hydration of the polymer.

By altering the properties of the polymer, the contributions of diffusion and/or polymer degradation to biologically active agent release can be controlled. For example, increasing the glycolide content of a poly(lactide-co-glycolide) polymer and decreasing the molecular weight of the polymer can enhance the hydrolysis of the polymer and thus, provides an increased biologically active agent release from polymer erosion.

The composition of this invention can be administered in vivo, for example, to a human, or to an animal, by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of biologically active agent based on the known parameters for treatment with the particular agent of the various medical conditions. As used herein, a "therapeutically effective amount", "prophylactically effective amount" or "diagnostically effective amount" is the amount of the biologically active agent or of the sustained release composition of biologically active agent needed to elicit the desired biological, prophylactic or diagnostic response following administration.

The invention will now be further and specifically described by the following examples which are not intended to be limiting.

EXEMPLIFICATIONS

Preparative Methods

Polymer

The polymer employed in the following examples was purchased from Alkermes, Inc. of Cincinnati, Ohio, and can be described as follows: poly(lactide-co-glycolide)(PLG); 50:50 lactide: glycolide ratio; 10kD Mol. Wt.; acid end groups (catalog no. 5050DL2A).

GENERAL PROCESS FOR PREPARING POLYMER/ACTIVE AGENT MATRIX PARTICLES

Formation of a mixture comprising a biocompatible polymer dissolved in a suitable polymer solvent and a biologically active agent.

Optional homogenization of the mixture.

Atomization of the mixture to form droplets.

Freezing of the droplets by contact with liquid nitrogen.

Extraction of the polymer solvent from frozen droplets into an extraction solvent (e.g., −80° C. ethanol) thereby forming a solid polymer/active agent matrix.

Isolation of the solid polymer/active agent matrix particles from the extraction solvent by filtration.

Removal of remaining solvent by evaporation.

Sizing of particles by passage through an appropriately sized mesh.

Annealing a substantial portion of the exterior surface of the solid polymer/active agent matrix particles.

SCANNING ELECTRON MICROSCOPY

Figure 1A:
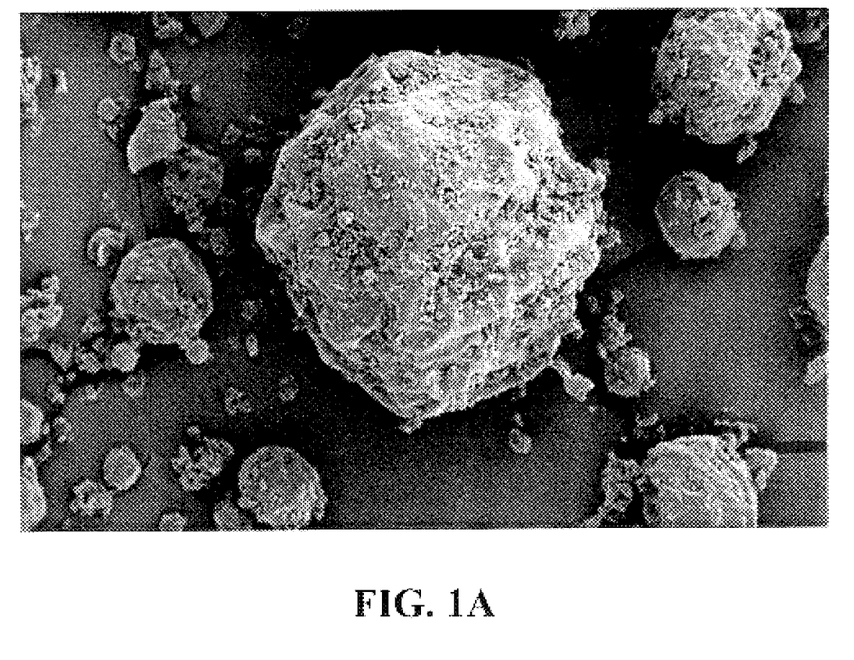
FIGS 1A–1C show scanning electron micrographs (SEMs) of placebo microparticles (no active agent) at 500× magnifications prepared as described herein, untreated (A), annealed under low heat conditions (B) and annealed under high heat conditions (C).
Figure 1B:
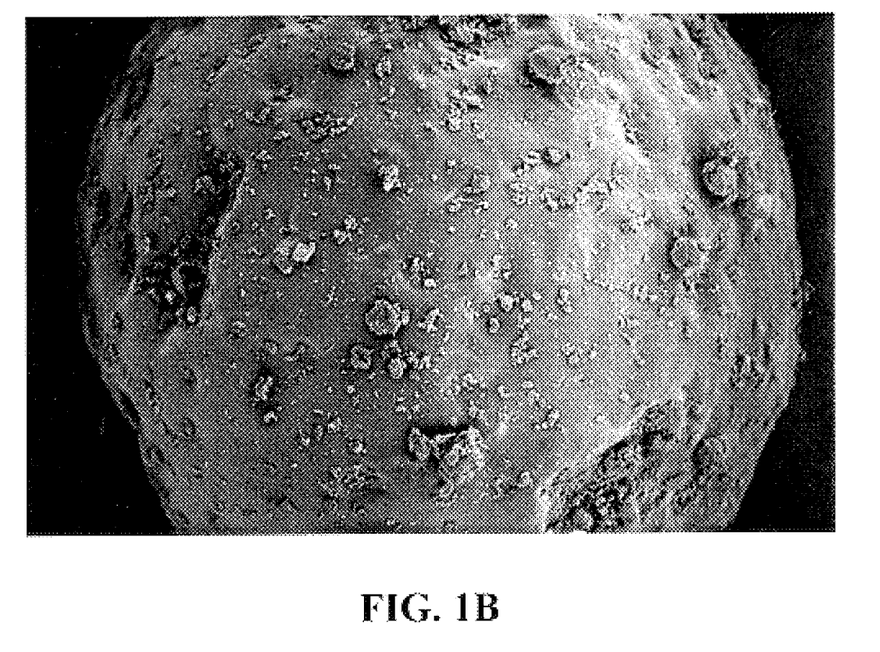
Figure 1C:
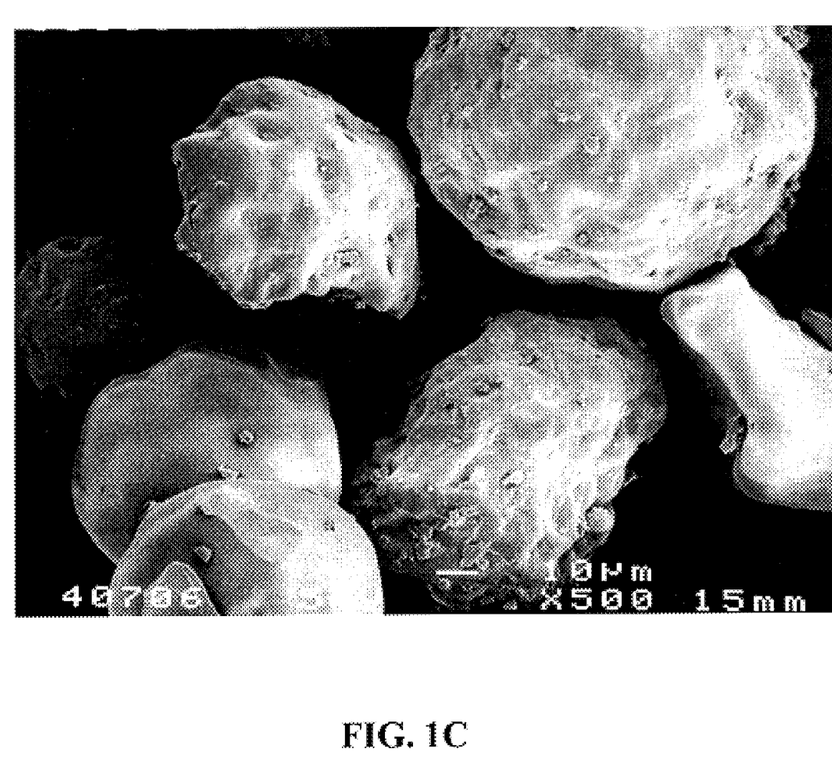
Figure 2A:
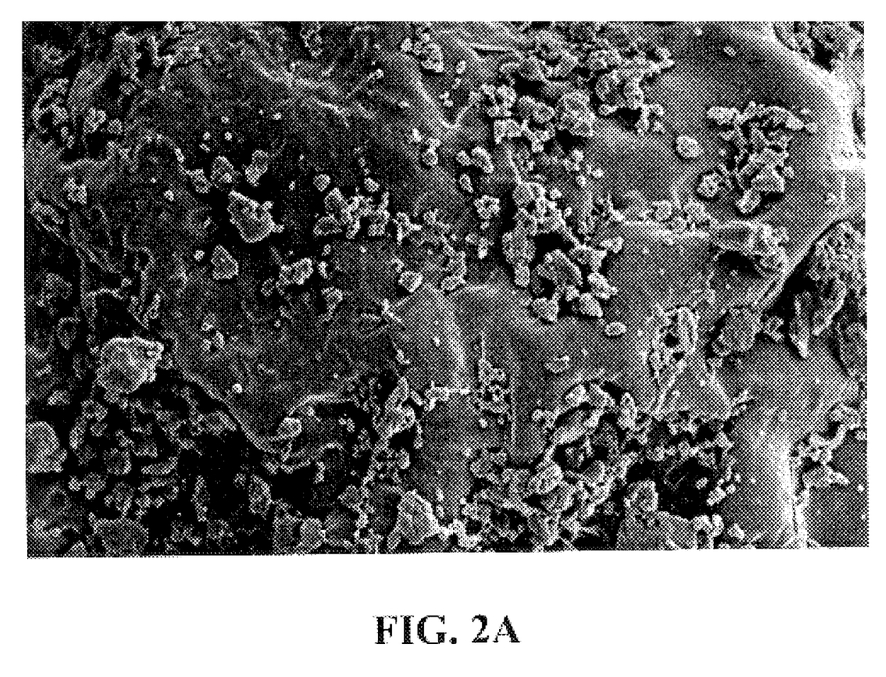
FIGS. 2A–2C show SEMs of placebo microparticles (no active agent) at 2000× magnifications prepared as described herein, untreated (A), annealed under low heat conditions (B) and annealed under high heat conditions (C).
Figure 2B:
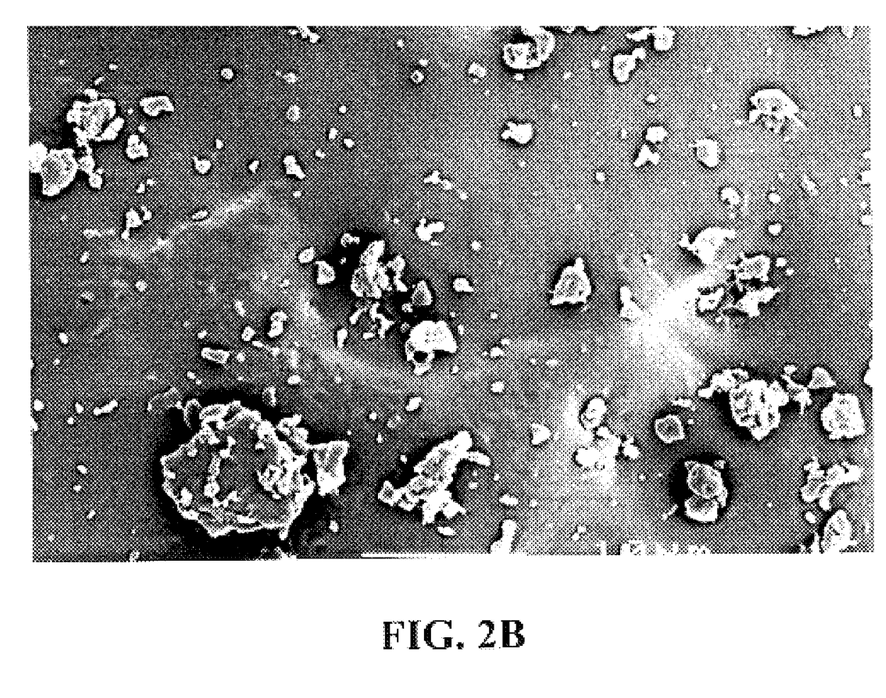
Figure 2C:
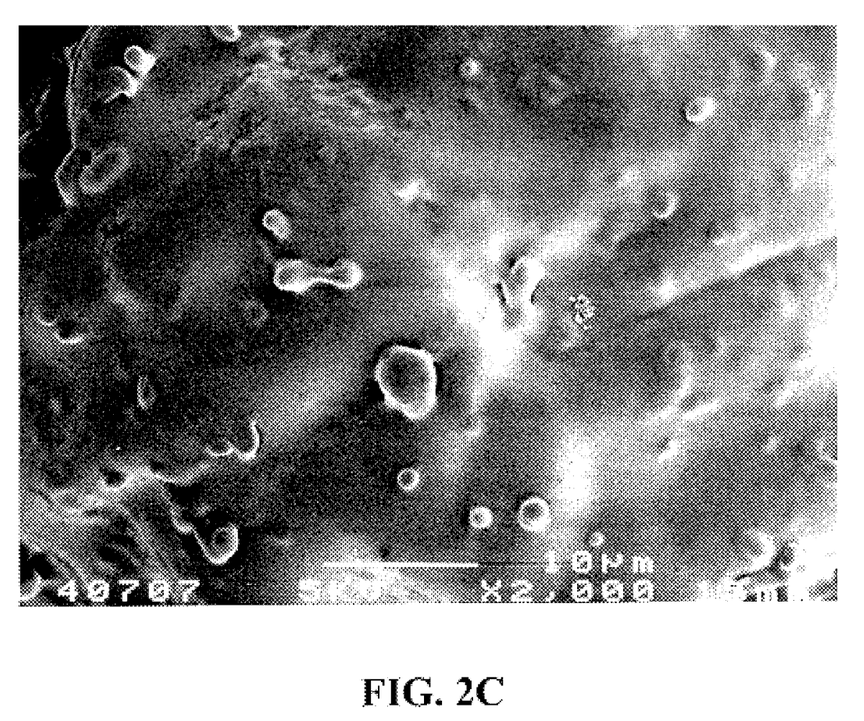
Figure 3A:
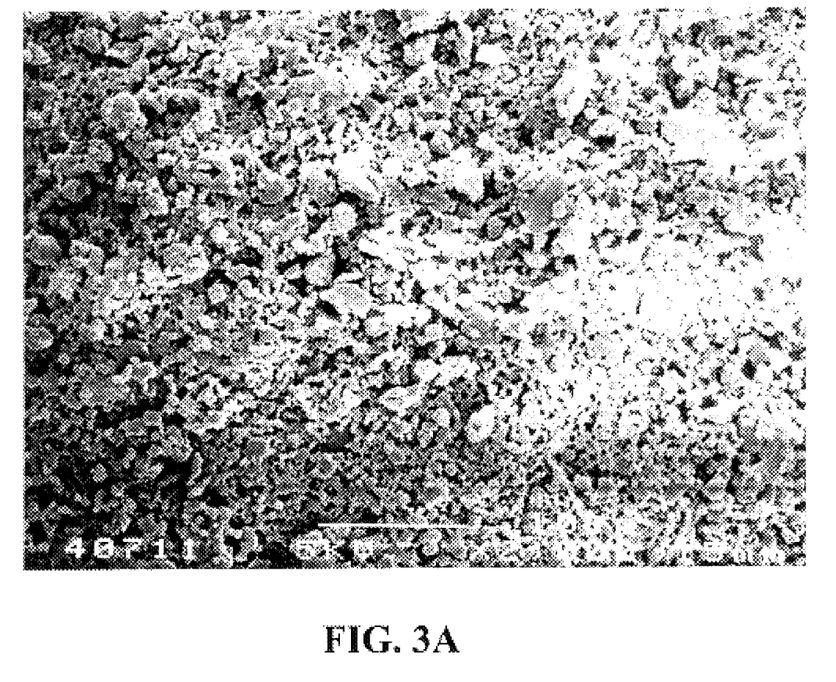
FIGS. 3A–3B show SEMs of BSA containing microparticles at 2000× magnification prepared as described herein which were either untreated (A) or annealed using acetone as the annealing solvent.
Figure 3B:
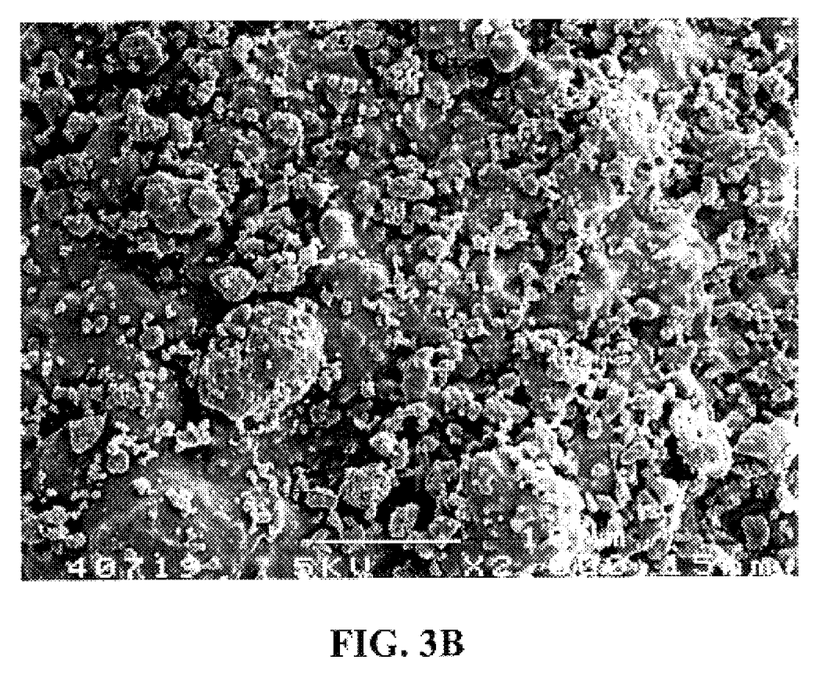

Scanning electron microscopy was conducted using a JEOL Model 6400 at a voltage of 5 kV. Samples were held in place with double-sided carbon tape affixed to an aluminum stub and sputter coated with a layer of gold. Photographs were taken at a magnifications of 500× and 2,000×. SEMs of placebo microparticles (no active agent) corresponding to no treatment, low heat annealing and high heat annealing, at the indicated magnifications, are illustrated in FIGS. 1A–1C and 2A–2C. In addition, SEMs of BSA containing microparticles corresponding to no treatment and acetone annealing, at a magnification of 2000×, are illustrated in FIGS. 3A–3B.

EXAMPLE 1

Preparation of BSA Containing Microparticles

The polymer used in the example was purchased from Alkermes, Inc. of Cincinnati, Ohio, and is a poly(lactide-co-glycolide) (PLG); 50:50 lactide:glycolide ratio; 10kD Mol. Wt.; esterified end groups.

Bovine Serum Albumin (BSA) containing microparticles were prepared according to the process outlined above, using 10% w/v solution of the PLG in methylene chloride, and a 2.5% w/v suspension of the BSA (available from JT Baker as Cat. #: JTA464-2) in the polymer solution.

EXAMPLE 2

Annealing of Microparicles

The BSA containing and placebo (no active agent) microparticles prepared as described above were annealed by either the application of heat or by the application of acetone using a Wurster type or bottom spray process.

The placebo microparticles were treated with heat under both high heat and low heat conditions. High heat conditions employed a fluidized bed temperature of about 58° C. Low heat conditions employed a fluidized bed temperature of about 38° C.

The run time for heat annealing of the microparticles at both high and low temperature conditions was approximately 20 minutes at the indicated temperature, spraying water into the system at 1 mL/min to reduce static. The air velocity in the fluidized bed system varied between 2–7 CFM.

The BSA containing microparticles were treating with acetone as the annealing solvent. The run time was about 30 minutes and the temperature of the fluidized bed system was ambient. The air velocity was between about 2–8 CFM. Acetone was sprayed at rate of 1.5 mL/min using a pressure of 10 psi.

EXAMPLE 3

Determination of in vitro Release

The annealed BSA containing microparticles thus formed were then tested for in vitro release properties. About 10 mg of microparticles were incubated in about 1500 uL of buffer (50 mM HEPES, 10 mM KCl, 0.1% NaN3, pH=7.2) at 37° C. After incubation for about 24 hours, a sample of the buffer was removed and BSA concentration determined by Biorad Protein Assay. The percent released was calculated by dividing the amount BSA released by the amount originally present in the microparticles. The results (average of duplicate measurements) are shown in the Table below.

| BSA Microparticle Treatment | % of Active Agent Released at 24 hours (±sd) |
| --- | --- |
| HEAT ANNEALED | 40.8 (1.7) |
| ACETONE ANNEALED | 37.2 (0.8) |
| NO TREATMENT-CONTROL | 44.5 (2.8) |

POROSITY MEASUREMENT METHODS

Samples were stored in glass vials over DRIERITE® in a vacuum desiccator at room temperature prior to helium pycnometery and nitrogen sorption.

HELIUM PYCNOMETERY: Solid density was determined using a Quantachrome Micro-Ultrapycnometer 1000 using the following conditions:

| | |
| --- | --- |
| Gas - Helium | Target Pressure - 18 psi |
| Cell Size - Large | Flow Purge - 1 min. |
| Sample Amount - 1.1 to 1.9 grams | Equilibrium Time - Auto |
| Max. Runs - 5 | Number of Runs Averaged - 3 |
| Deviation Requested - 0.500% | Temperature - Ambient |

Densities were determined for the untreated microparticles and microparticles treated at 38° C. or 58° C. for 20 minutes. Densities were measured at 1.37 g/cc for untreated microparticles, 1.34 g/cc for microparticles treated at low heat conditions and 1.31 g/cc for microparticles treated at high heat conditions.

NITROGEN SORPTION: Nitrogen sorption experiments were performed on a Quantachrome NOVA 2000. Sample cells were large pellet cells with 12-mm stems. All samples were vacuum degassed at room temperature, overnight, prior to nitrogen sorption. The specific surface area was determined in the BET region of the adsorption isotherm. Measurements of relative pressure were acquired at P/Po values of 0.1, 0.15, 0.2 and 0.3. The total pore volume was determined at P/Po=0.99. Specific surface areas were determined using the Quantachrome NOVA 2000 data reduction software for the untreated microparticles and microparticles following treatment at either 38° or 58° C. for 20 minutes.

Conditions:
Adsorption Equilibrium Tolerance=0.1 mm/Hg
Adsorption Equilibrium Time=150 sec.
Adsorption Maximum Dwell Time =300 sec.
Bath Temperature=77.40 K
Sample Amount=1.8 to 2.9 grams
Po was calculated as described above.

EXAMPLE 4

Specific surface areas were determined for untreated microparticles and microparticles following treatment at either 38° or 58° C. for 20 minutes. The specific surface area for the untreated microparticles was 5.4891 $m^2/g$. Microparticles treated for 20 minutes at 38° C. had a specific surface area of 0.2742 $m^2/g$. The measured reduction in surface area was consistent with the results seen in the SEMs showing a smoother, non-porous surface following treatment. Measurements of the microparticles treated for 20 minutes at 58° C. demonstrated an even lower specific surface area of [31] 0.0135 $m^2/g$. The negative specific surface area generated by the data reduction software reflects the limit of detection of the measurements, but is consistent with the trend towards smoother, non-porous surfaces as seen in the SEMs following the higher temperature treatment.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

What is claimed is:

1. A method for preparing a composition for the sustained release of a biologically active agent, comprising the steps of:
   a) forming a mixture comprising a biologically active agent, a biocompatible polymer, and a polymer solvent;
   b) removing the polymer solvent thereby forming a solid polymer/active agent matrix; and
   c) annealing at least a substantial portion of the exterior surface of the polymer/active agent matrix by the application of an annealing solvent.

2. The method of claim 1 wherein annealing is accomplished by the application of an annealing solvent to the polymer/active agent matrix in a fluidized bed system.

3. The method of claim 2 wherein the fluidized bed system is a bottom spray system.

4. The method of claim 1 wherein the annealing solvent is selected from the group consisting of: methylene chloride, chloroform, acetone, ethyl acetate, anisole, methyl acetate, hexafluoroisopropanol, tetrahydrofuran, dimethylsulfoxide and any combination thereof.

5. The method of claim 1 wherein the temperature of the fluidized bed is below the flashpoint and above the freezing point of the annealing solvent.

6. The method of claim 1 wherein the polymer/active agent matrix is in the form of microparticles.

7. The method of claim 1 wherein about 25% or more of the exterior surface is annealed.

8. The method of claim 1 wherein about 40% or more of the exterior surface is annealed.

9. The method of claim 1 wherein between about 50% and about 100% of the exterior surface is annealed.

10. The method of claim 1 further comprising the steps of: forming droplets of the polymer/active agent mixture and freezing the droplets of the polymer/active agent mixture, wherein said forming and freezing steps are performed prior to removing the polymer solvent.

11. The method of claim 10 wherein the droplets are microdroplets.

12. The method of claim 1 wherein the biocompatible polymer is biodegradable.

13. The method of claim 12 wherein the biodegradable polymer is selected from the group consisting of poly (lactide)s, poly(glycolide)s, poly(lactide-coglycolide)s, poly (lactic acid)s, poly(glycolic acid)s, poly(lactic acid-co-glycolic acid)s, poly(caprolactone), polycarbonates, polyesteramides, polyanhydrides, poly(amino acid)s, poly (ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

14. The method of claim 13 wherein said polymer is poly(lactide-co-glycolide).

15. The method of claim 1 wherein the biocompatible polymer is non-biodegradable.

16. The method of claim 1 wherein the polymer solvent is methylene chloride, chloroform, acetone, ethyl acetate, anisole, methyl acetate, dimethylsulfoxide, hexafluoroisopropanol or any combinations thereof.

17. The method of claim 1 wherein the biologically active agent is a protein, peptide or nucleic acid.

* * * * *